United States Patent
Gregg et al.

(10) Patent No.: US 11,963,800 B2
(45) Date of Patent: Apr. 23, 2024

(54) ECG TRAINING AND SKILL ENHANCEMENT

(71) Applicant: KONINKLIJKE PHILIPS N.V., Eindhoven (NL)

(72) Inventors: Richard Earl Gregg, Westford, MA (US); Saeed Babaeizadeh, Arlington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 921 days.

(21) Appl. No.: 16/093,327

(22) PCT Filed: Apr. 14, 2017

(86) PCT No.: PCT/EP2017/059049
§ 371 (c)(1),
(2) Date: Oct. 12, 2018

(87) PCT Pub. No.: WO2017/178643
PCT Pub. Date: Oct. 19, 2017

(65) Prior Publication Data
US 2019/0175118 A1    Jun. 13, 2019

Related U.S. Application Data

(60) Provisional application No. 62/349,809, filed on Jun. 14, 2016, provisional application No. 62/323,616, filed on Apr. 15, 2016.

(51) Int. Cl.
G16H 50/50    (2018.01)
A61B 5/00    (2006.01)
(Continued)

(52) U.S. Cl.
CPC .............. *A61B 5/7246* (2013.01); *A61B 5/25* (2021.01); *A61B 5/318* (2021.01); *A61B 5/7264* (2013.01);
(Continued)

(58) Field of Classification Search
CPC ... A61B 5/7246; A61B 5/0402; A61B 5/0408; A61B 5/7264; A61B 5/7267;
(Continued)

(56) References Cited

U.S. PATENT DOCUMENTS 6,171,256 B1    1/2001  Hampton
6,358,214 B1 *  3/2002  Tereschouk .......... A61B 5/0402
                                                  600/508

(Continued)

FOREIGN PATENT DOCUMENTS

JP    2007279942 A    10/2007

OTHER PUBLICATIONS

Buza, K. et al., "Fast classification of electrocardiograph signals via instance selection", Healthcare Informatics, Imaging and Systems Biology (HISB), 2011 First IEEE International Conference on, IEEE, Jul. 26, 2011, pp. 9-16.

(Continued)

*Primary Examiner* — Ankit D Tejani
*Assistant Examiner* — Joshua Brendon Solomon

(57) ABSTRACT

A diagnostic electrocardiogram system employing an electrode lead system (40) for generating one or more electrode signals indicative of electrical activity of a subject heart (10). The diagnostic electrocardiogram system further employs a diagnostic electrocardiograph (50) coupled to the electrode lead system (40) for communicating (e.g., listing, displaying and/or printing a subject electrocardiogram (20) and one more diagnostic electrocardiograms (30) designated as a morphology match to the subject electrocardiogram (Continued)

(20). The subject electrocardiogram (20) includes one or more interpretations of ECG features derived from tire electrical activity of the subject heart (10) as indicated by tire electrode signal(s) (e.g., an algorithmic interpretation and/or an electrocardiographer interpretation of the subject electrocardiogram (20)). The diagnostic electrocardiogram(s) includes one or more diagnoses of ECG features derived from recorded electrical activity of diagnosed heart(s) (11) (e.g., an algorithmic diagnosis and/or an electrocardiographer diagnosis of the diagnostic electrocardiogram(s) (30)).

20 Claims, 10 Drawing Sheets

(51) Int. Cl.
  *A61B 5/25* (2021.01)
  *A61B 5/318* (2021.01)
  *G01N 21/359* (2014.01)
  *G16H 30/20* (2018.01)
  *G16H 50/70* (2018.01)
  *G16H 70/20* (2018.01)
  G16H 50/20 (2018.01)

(52) U.S. Cl.
  CPC ......... *A61B 5/7267* (2013.01); *G01N 21/359* (2013.01); *G16H 30/20* (2018.01); *G16H 50/50* (2018.01); *G16H 50/70* (2018.01); *G16H 70/20* (2018.01); *G16H 50/20* (2018.01)

(58) Field of Classification Search
  CPC ........ G16H 50/50; G16H 50/70; G16H 50/20; G16H 30/20; G16H 70/20; G01N 21/359
  See application file for complete search history.

(56) References Cited

U.S. PATENT DOCUMENTS

| | | | |
|---|---|---|---|
| 7,996,073 | B2 | 8/2011 | Busche |
| 8,543,193 | B2 | 9/2013 | Satin |
| 10,211,180 | B2 | 2/2019 | Schmidt |
| 2003/0163355 | A1* | 8/2003 | Kaiser .................. G06Q 10/10 705/3 |
| 2008/0103403 | A1 | 5/2008 | Cohen |
| 2011/0137190 | A1* | 6/2011 | Katz ..................... A61B 5/04 600/509 |
| 2012/0041277 | A1 | 2/2012 | Ebadollahi |

OTHER PUBLICATIONS

Fisch, C. et al. Clinical Competence in Electrocardiography. A Statement for Physicians from the ACP/ACC/AHA Task Force on Clinical Privileges in Cardiology. Circulation. 1995; 91: 2683-2686.

* cited by examiner

ECG TRAINING AND SKILL ENHANCEMENT

This application is a national stage application under 35 U.S.C. § 371 of International Application No. PCT/EP2017/059049 filed on Apr. 14, 2017 and published in the English language on Oct. 19, 2017 as International Publication No. WO2017/178643, which claims priority to U.S. Patent Application Nos. 62/349,809 and 62/323,616 filed on Jun. 14, 2016 and Apr. 15, 2016, respectively, the entire disclosures of which are incorporated herein by reference.

FIELD OF THE INVENTION

The present disclosure relates generally to electrocardiogram (ECG) training and skill enhancement, and more particular to systems, devices and methods for ECG training and skill enhancement by communicating (e.g., displaying, printing, linking, etc.) morphology matching ECGs from a training ECG set.

BACKGROUND OF THE INVENTION

The skill of reading n-lead ECG (e.g., 12-lead ECG) typically starts with textbook examples and explanation of the ECG phenomena. More skill typically comes with supervised reading of ECG. ECG skill typically is further enhanced with practice and feedback from experts. At some point, there is no ready feedback and the electrocardiographer is on his/her own. Examples of an electrocardiographer include, but is not limited to, physicians, nurse practitioners, physician assistants, nurses, paramedics, medical assistants, trained nursing assistants and emergency medical technicians.

More particular, diagnostic ECG interpretation or "reading" an ECG is typically a skill that takes considerable time and practice to truly master. There is a large body of knowledge related to the technical aspects of ECG and most importantly, the reflection of many cardiac disorders in the ECG signal. ECG training typically starts with textbook explanations of where the signal comes from, how it is recorded and how signals from the four chambers appear in the ECG signal. The textbook instruction typically includes example ECGs in the main areas of arrhythmia and signal morphology which relates to conditions such as conduction system problems and infarction and ischemia. Some on-the-job training typically completes the training, which is typically verified with nursing or medical boards.

The problem is that training typically does not continue. Moreover, electrocardiographers usually do not get feedback on the quality or correctness of their ECG interpretation. In addition, patients frequently have a long list of comorbidities with a confusing mixture of effects simultaneously present in the ECG. Textbook ECG examples almost never include mixtures of effects because it is confusing for beginner electrocardiographers.

Electrocardiographers would benefit from a set of example ECGs to be able to look up similar ECGs to the types they do not see frequently. The problem is that the example ECGs are typically organized by ECG interpretation. Therefore, one must know the interpretation already to find a similar example.

ECG currently is the most common cardiac investigation provided in many settings including primary care, in the field or on the ambulance for suspected heart condition patients, etc. Although it is accepted as core medical practice, it is believed that only a low percentage of electrocardiographers receive formalized training and assessment in interpreting ECGs. In recent years, many electrocardiographers rely on computer algorithms to interpret the ECG for them. However, such algorithms are not perfect as they usually do not have access to the clinical context and other needed information to reliably make an accurate diagnostic. This is why, it is often mandatory in the clinical setting that all computer-interpreted ECGs be verified and appropriately corrected by an experienced electrocardiographer. More particular, although many physicians acquire the cognitive skills needed for proper interpretation of the ECG, e.g., during a fellowship or a residency program, completion of a fellowship or residency does not guarantee competence. The present disclosure can help electrocardiographers to continue their training on the job and get help with those ECGs difficult to interpret. As one having ordinary skill in the art shall appreciate in view of teachings herein, the present disclosure can have numerous other benefits too.

SUMMARY OF THE INVENTION

The present disclosure helps an electrocardiographer (e.g., a physician, a nurse practitioner, a physician assistant, a nurse, a paramedic, a medical assistant, a trained nursing assistants and an emergency medical technicians) continue to improve his/her ECG reading skills by, e.g., offering (and/or providing, displaying, printing or otherwise communicating) a set of similar ECGs for (virtually) every (or most and/or a predefined number or percentage) ECG interpreted or "read", e.g., in a particular environment or as otherwise may be available to be tracked, stored, processed etc. Generally, it is preferable to have a relatively large number of ECGs in the training set.

In accordance with exemplary embodiments of the present disclosure, in the main application of electronic ECG editing, the inventions of the present disclosure provide and electrocardiographer with example ECGs that are similar to the ECG they are currently editing or viewing. The inventions of the present disclosure select similar ECGs by characteristics of the signal, not by correct interpretation. In that way, the electrocardiographer can see many ECGs that have a similar look but potentially different ECG interpretation because many ECG characteristics have a set of possible differential diagnoses. Not only can the electrocardiographer see differential diagnosis possibilities, they can also see the opinions of different electrocardiographers for similar ECGs because the database consists of prior ECGs from their and/or associated institution(s). In addition, the inventions of the present disclosure can provide the probability that the ECG in question is in a particular diagnostic category, such as, for example, left bundle branch block (LBBB), right bundle branch block (RBBB), left ventricular hypertrophy, right ventricular hypertrophy, left anterior fascicular block, acute myocardial infarction, prior myocardial infarction, and many others. Only the higher probabilities may be presented to the user.

One form of the inventions of the present disclosure is a diagnostic electrocardiogram system employing an electrode lead system for generating one or more electrode signals indicative of electrical activity of a subject heart. The diagnostic electrocardiogram system further employs a diagnostic electrocardiograph coupled to the electrode lead system for communicating a subject electrocardiogram and one or more diagnostic electrocardiograms determined by the diagnostic electrocardiograph as a morphology match to the subject electrocardiogram (e.g., a linking, displaying, and/or printing the morphology matched subject electrocardiogram and the diagnostic electrocardiogram(s)). The subject electrocardiogram includes one or more interpretations of ECG features derived from the electrical activity of the subject heart as indicated by the electrode signal(s) (e.g., an algorithmic interpretation and/or an electrocardiographer interpretation of the subject electrocardiogram). The diagnostic electrocardiogram(s) includes one or more diagnoses of ECG features derived from recorded electrical activity of the diagnosed heart(s) (e.g., an algorithmic diagnosis and/or an electrocardiographer diagnosis of the diagnostic electrocardiograms(s)).

The designation by the diagnostic electrocardiograph may be accomplished by the diagnostic electrocardiograph navigating a cluster tree constructed from a training set of diagnostic electrocardiograms whereby the dimensional space of the cluster tree is derived from a linear regression modeling of ECG features of the training set of diagnostic electrocardiograms.

A second form of the inventions of the present disclosure is the aforementioned electrocardiograph employing a subject ECG controller for controlling a generation of the subject electrocardiogram. The electrocardiograph further employs a diagnostic electrocardiogram controller for controlling a determination of the diagnostic electrocardiogram(s) as a morphology match to the subject electrocardiogram.

A third form of the inventions of the present disclosure is a diagnostic electrocardiograph method involving the diagnostic electrocardiograph communicating the subject electrocardiogram informative of one or more interpretations of ECG features derived from the electrical activity of the subject heart as indicated by electrode signal(s) generated by a lead system. The diagnostic electrocardiograph method further involves diagnostic electrocardiograph further communicating the diagnostic electrocardiogram(s) determined by the diagnostic electrocardiograph as a morphology match to the subject electrocardiogram (e.g., a linking, displaying, and/or printing of the subject electrocardiogram and the morphology matched diagnostic electrocardiogram(s)). The diagnostic electrocardiogram(s) include(s) one or more diagnoses of ECG features derived from recorded electrical activity of diagnosed heart(s).

For purposes of the present disclosure, the term "electrocardiograph" broadly encompasses all devices, known prior to and subsequent to the present disclosure, for recording the electrical activity of a heart over a period of time, and the term "ECG device" broadly encompasses all stand-alone electrocardiographs and devices/systems incorporating an electrocardiograph including, but not limited to:
(1) diagnostic ECG devices (e.g., PageWriter TC cardiographs, Efficia series of cardiograph);
(2) exercise ECG devices (e.g., ST80i stress testing system);
(3) ambulatory ECG devices (Holter monitor);
(4) bed-side monitoring ECG device (e.g., IntelliVue monitors, SureSigns monitors, and Goldway monitors);
(5) hemodynamic monitoring (e.g., per Flex Cardio Physiomonitoring system);
(6) telemetry ECG device (e.g., IntelliVue MX40 monitor);
(7) automated external defibrillator and advanced life support products (e.g., HeartStart MRx and HeartStart XL defibrillators, and Efficia DFM100 defibrillator/monitor);
(8) ECG management system (e.g., IntelliSpace ECG management system); and
(9) central monitoring system (e.g., PIIC iX and IntelliVue IL central monitoring systems).

Also for purposes of the present disclosure,
(1) the term "diagnostic electrocardiograph" broadly encompasses all electrocardiographs having a structural configuration incorporating inventive principles of the present disclosure as exemplary described herein, and the term "diagnostic electrocardiograph method" broadly encompasses all methods for training and/or operating a diagnostic electrocardiograph that incorporate the inventive principles of the present disclosure as exemplary described herein;
(2) terms of the art including, but not limited to, "electrocardiographer", "electrode", "electrocardiogram", "ECG features", "interpretation", "diagnosis", "linear regression" and "cluster tree" are to be interpreted as understood in the art of the present disclosure and as exemplary described herein;
(3) more particular to the inventions of the present disclosure, the term "electrocardiogram" broadly encompasses, as understood in the art of the present disclosure and as exemplary described herein, all types of cardiograms for recording an electrical activity of the heart including, but not limited, to a 12-lead electrocardiogram and 3-lead vectorcardiogram;
(4) the descriptive labeling for the term "electrocardiogram" herein as a "subject electrocardiogram" or as a "diagnostic electrocardiogram" facilitates a distinction between electrocardiograms as described and claimed herein without specifying or implying any additional limitation to the term "electrocardiogram";
(5) more particular to the inventions of the present disclosure, the term "interpretation" broadly encompasses, as understood in the art of the present disclosure and as exemplary described herein, one or more proposed explanation(s) of a normality and/or an abnormality of a morphology of an electrocardiogram as would be understood by those skilled in the art of the present disclosure. Examples of an interpretation of an electrocardigoram include, but are not limited to, an algorithmic interpretation of the electrocardiogram generated by an electrocardiograph and an electrocardiographer interpretation of the electrocardiogram annotated by an electrocardiographer;
(6) more particular to the inventions of the present disclosure, the term "diagnosis" broadly encompasses, as understood in the art of the present disclosure and as exemplary described herein, one or more formalized statement(s) of a normality and/or an abnormality of a morphology of an electrocardiogram as would be understood by those skilled in the art of the present disclosure. Examples of a diagnosis of an electrocardiogram include, but are not limited to, an enactment, a confirmation, an approval, an acceptance, etc. of an algorithmic interpretation of the electrocardiogram generated by an electrocardiograph and of an electrocardiographer interpretation of the electrocardiogram annotated by an electrocardiographer;
(7) more particular to the inventions of the present disclosure, the term "inexpensive ECG features" broadly encompasses, as understood in the art of the present disclosure and as exemplary described herein, global features and per-lead features of an electrocardiogram including, but not limited to, a QRS axis, a QRS duration, a QT interval, a Q/R/S wave amplitude, ST-segment amplitude, T-wave amplitude, and vector loop.
(8) more particular to the inventions of the present disclosure, the term "expensive ECG features" broadly encompasses, as understood in the art of the present disclosure and as exemplary described herein, ECG features derived from a comparable processing of multiple electrocardiograms including, but not limited to, a template matching, a cross correlation and a RMS difference between electrocardiograms.

(9) the term "feature vector" broadly encompasses, as understood in the art of the present disclosure and as exemplary described herein, a m-dimensional vector of ECG feature(s), m≥1 or a vector loop;

(10) the term "morphology match" broadly encompasses, as understood in the art of the present disclosure and as exemplary described herein, similarity of ECG feature(s) between corresponding electrode signal(s) of a pair of electrocardiograms with the ECG feature(s) being characteristic of a shape of the electrocardiograms;

(11) the term "diagnostic category" broadly encompasses, as understood in the art of the present disclosure and as exemplary described herein, a category representative of a particular diagnostic assessment of an electrocardiogram. Examples of a diagnostic category include, but are not limited to, (a) ventricular conduction defect including interpretation left anterior fascicular block, left bundle branch block (LBBB), and right bundle branch block (RBBB), (b) hypertrophy including interpretation left ventricular hypertrophy, right ventricular hypertrophy, (c) ischemia and infarction including interpretation acute myocardial infarction, prior myocardial infarction and subendocardial ischemia.

(12) the term "accurate diagnosis probability" broadly encompasses, as exemplary described herein, a probability a particular diagnostic category represents an accurate diagnostic assessment of an electrocardiogram;

(13) the term "controller" broadly encompasses all structural configurations, as understood in the art of the present disclosure and as exemplary described herein, of an application specific main board or an application specific integrated circuit housed within or linked to an electrocardiograph for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s). Any descriptive labeling of a controller herein (e.g., a "subject ECG" controller and a "diagnostic ECG" controller) serves to identify a particular controller as described and claimed herein without specifying or implying any additional limitation to the term "controller";

(14) the term "application module" broadly encompasses a component of the controller including an electronic circuit and/or an executable program (e.g., executable software and/o firmware stored on non-transitory computer readable medium(s) for executing a specific application. Any descriptive labeling of an application module herein (e.g., a "ECG feature extractor" module and a "cluster tree generator" module) serves to identify a particular application module as described and claimed herein without specifying or implying any additional limitation to the term "application module";

(15) the terms "communicating" broadly encompasses all communication schemes utilized by an electrocardiograph known prior to, concurrently with and subsequently to the present disclosure for conveying an electrocardiogram to a user of the electrocardiograph. Examples of such communication schemes include, but are not limited, providing a link to the electrocardiogram, a display of the electrocardiogram and a printing of the electrocardiogram;

(16) the terms "signal" and "data" broadly encompasses all forms of a detectable physical quantity or impulse (e.g., voltage, current, or magnetic field strength) as understood in the art of the present disclosure and as exemplary described herein for transmitting information in support of applying various inventive principles of the present disclosure as subsequently described herein;

(17) any descriptive labeling for the term "signal" herein facilitates a distinction between signals as described and claimed herein without specifying or implying any additional limitation to the term "signal"; and

(17) any descriptive labeling for the term "data" herein facilitates a distinction between data as described and claimed herein without specifying or implying any additional limitation to the term "data".

The foregoing forms and other forms of the inventions of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

Figure 1A:
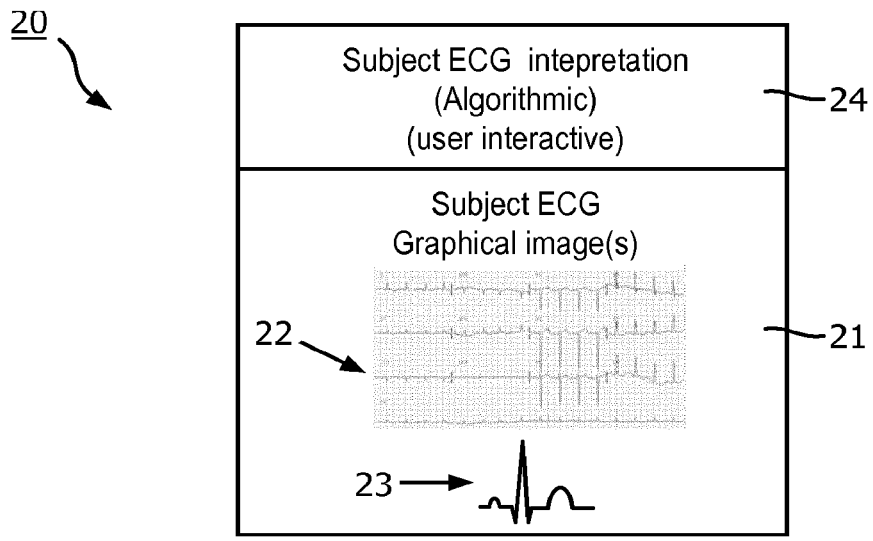
FIG. 1A illustrates an exemplary embodiment of a subject electrocardiograms in accordance with the inventive principles of the present disclosure and FIG. 1B illustrates an exemplary embodiment of a diagnostic electrocardiograms in accordance with the inventive principles of the present disclosure.
Figure 1A:
Figure 1B:
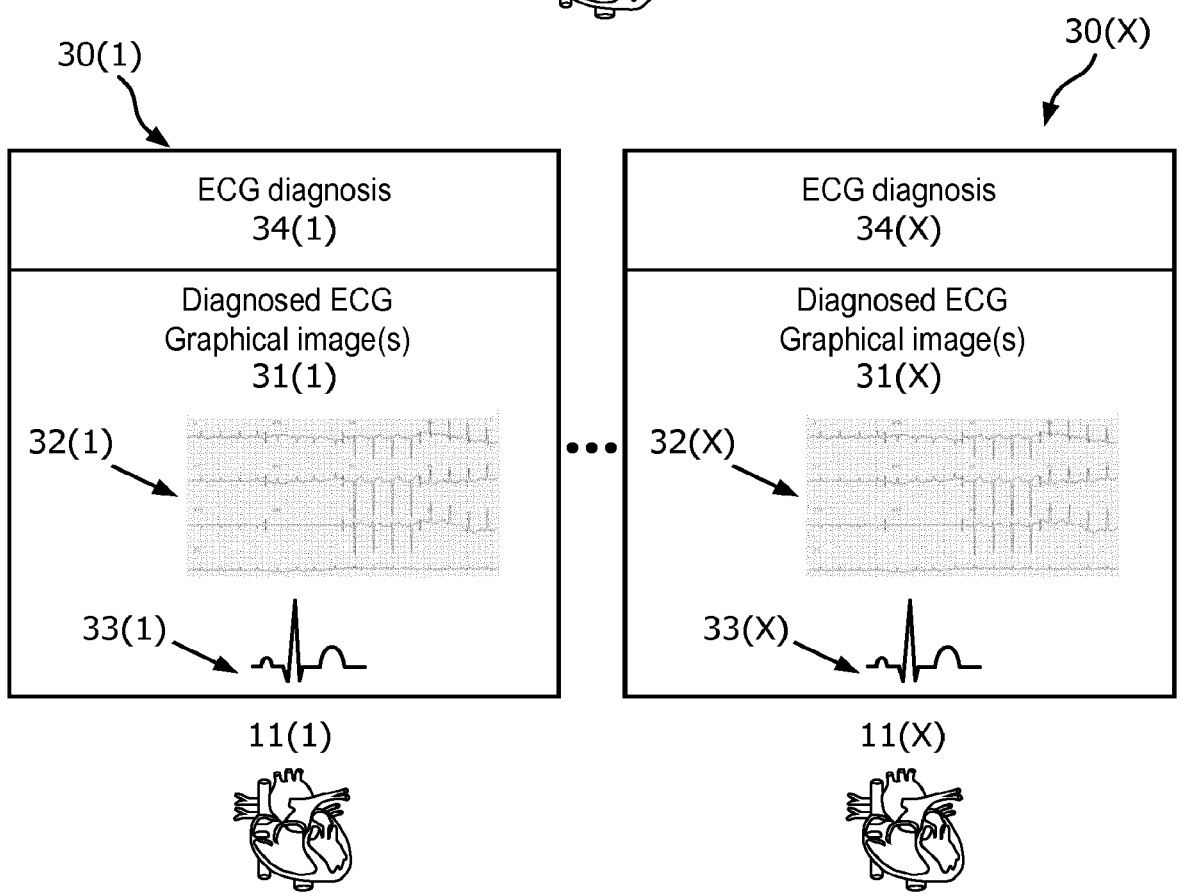

To facilitate an understanding of the present disclosure, the following description of FIGS. 1A and 1B teaches inventive principles of a diagnostic electrocardiogram of the present disclosure as compared to a subject electrocardiogram as known in the art of the present disclosure. More particular, the present disclosure is premised on a designation by an electrocardiograph of one or more diagnostic electrocardiograms as a morphology match to a subject electrocardiogram with the subject electrocardiogram being generated from a current ECG monitoring and/or testing by the electrocardiograph of a subject heart and with the diagnostic electrocardiogram(s) being generated from previously diagnosed ECG monitoring and/or testing of non-subject heart(s) (i.e., diagnosed heart(s)). From the description of FIGS. 1A and 1B, those having ordinary skill in the art of the present disclosure will appreciate how to apply the inventive principles of the present disclosure for making and using numerous and various embodiments of a diagnostic electrocardiogram of the present disclosure.

Referring to FIG. 1A, a subject electrocardiogram 20 is an example of a subject electrocardiogram that may be communicated (e.g., displayed, printed, linked, etc.) by an electrocardiograph during an ECG monitoring and/or testing of a subject heart 10 via any type of lead system as known in the art of the present disclosure (e.g., a 12 lead system, a 3-lead system, etc.). Subject electrocardiogram 20 as communicated by the electrocardiograph includes graphical image(s) 21, such as, for example, a 12-lead ECG 22 as known in the art of the present disclosure, a ECG waveform 23 generated as known in the art of the present disclosure, and a vectorcardiogram (not shown) as known in the art of the present disclosure. The exemplary subject electrocardiogram 21 further includes a textual interpretation 24 of a normality or an abnormality of an ECG morphology of graphical image(s) 21 generated by an interpretation algorithm executed by the diagnostic electrocardiograph as known in the art of the present disclosure and/or by an annotated interpretation by an electrocardiographer via a graphical user interface of the associated electrocardiograph as known in the art of the present disclosure. More particularly, interpretation 24 is directed to one or more proposed explanation(s) of the normality or the abnormality of the ECG morphology of graphical image(s) 21 as would be understood by those skilled in the art of the present disclosure.

Referring to FIG. 1B, diagnostic electrocardiograms 30 are examples of an X number of diagnostic electrocardiogram(s), X≥1, that may be communicated (e.g., displayed or printed) by the electrocardiograph during the aforementioned ECG monitoring and/or testing of subject heart 10. Each diagnostic electrocardiogram 30 was generated from a previous diagnosed ECG monitoring and/or testing of a non-subject heart 11 (i.e., a diagnosed heart) via any type of lead system as known in the art of the present disclosure (e.g., a 12 lead system, a 3-lead system, etc.).

Each diagnostic electrocardiogram 30 as communicated by the electrocardiograph includes graphical image(s) 31, such as, for example, a 12-lead ECG 32 as known in the art of the present disclosure, an ECG waveform 33 generated as known in the art of the present disclosure or a vectorcardiogram as known in the art of the present disclosure. The exemplary diagnostic electrocardiograms 31 further include a textual diagnosis 34 by an electrocardiographer of a normality and/or an abnormality of the ECG morphology of graphical image(s) 31. Each ECG diagnosis 34 is directed to one or more formalized explanations of the normality and/or the abnormality of the ECG morphology of corresponding graphical image(s) 31 as would be understood by those skilled in the art of the present disclosure (e.g., an enactment, a confirmation, an approval, an acceptance, etc. of an interpretation of the diagnostic electrocardiogram).

By simultaneously communicating a subject electrocardiogram (e.g., subject electrocardiogram 20 as shown in FIG. 1A) and one or more diagnostic electrocardiograms (e.g., diagnostic electrocardiograms 30 as shown in FIG. 1B) designated as a morphology match to the subject electrocardiogram, the present disclosure improves upon an electrocardiograph's capability to facilitate an accurate diagnosis by an electrocardiographer of the subject electrocardiogram.

Figure 2:
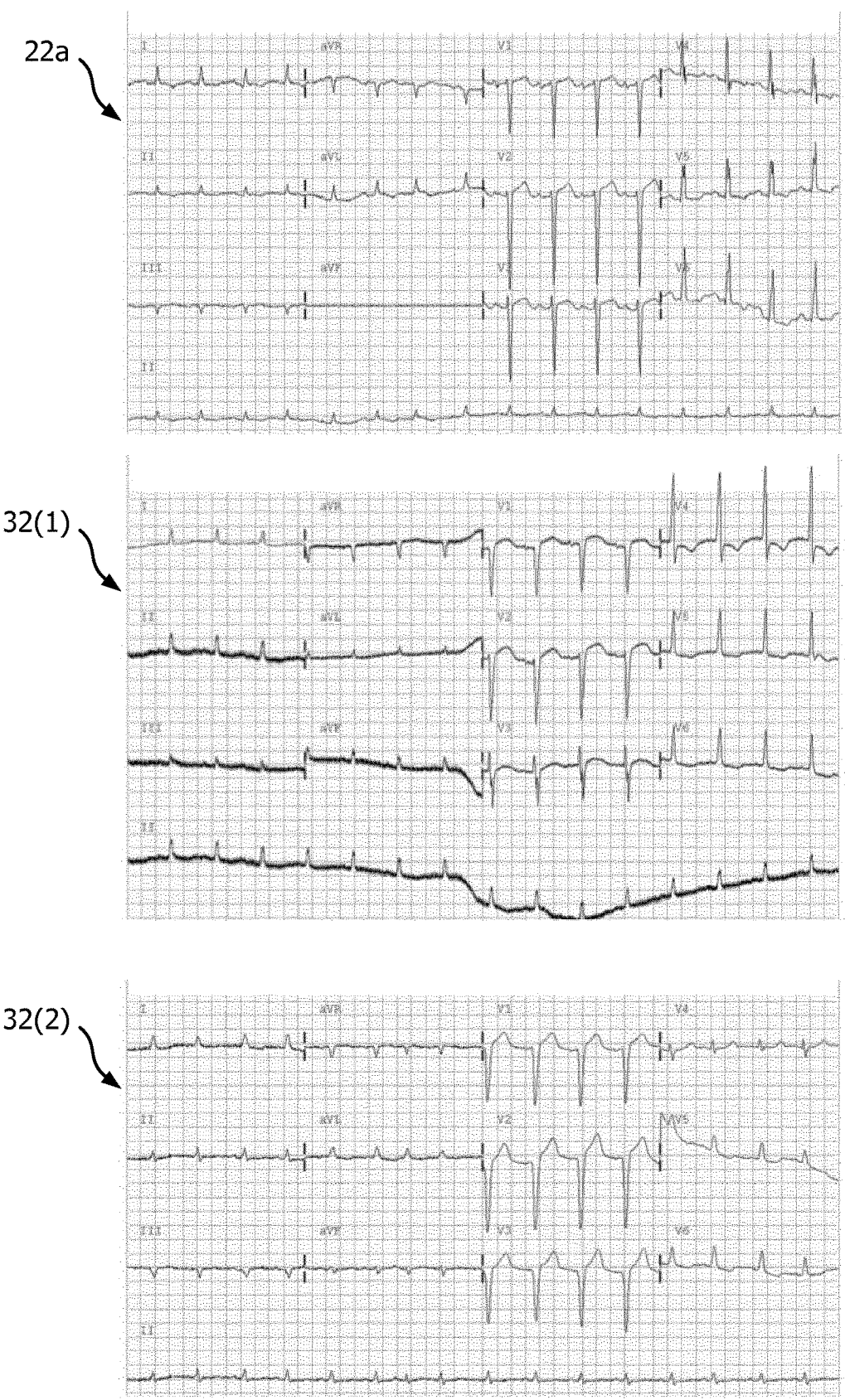
FIG. 2 illustrates exemplary embodiments of a subject ECG and a pair of diagnostic ECGs in accordance with the inventive principles of the present disclosure.

For example, FIG. 2 illustrates an exemplary 12-lead ECG 22a of a subject electrocardiogram having an ECG morphology of the QRS in leads V1 through V4 that could be interpreted, algorithmically and/or via annotation, as a left bundle branch block, a left ventricular hypertrophy or a prior myocardial infarction. These possible interpretations of 12-lead ECG 22a make it difficult for anelectrocardiographer to render a diagnosis of the morphology of 12-lead ECG 22a, particularly an inexperienced electrocardiographer.

FIG. 2 further illustrates 12-lead ECGs 32(1) and 32(2) of a pair of diagnostic electrocardiograms designated by the electrocardiograph, from a sample database of roughly 10,000 diagnostic electrocardiograms, as a morphology match in view of ECG morphology of the QRS in leads V1 through V4 of 12-lead ECGs 32(1) and 32(2) essentially being the same as the ECG morphology of the QRS in leads V1 through V4 of 12-lead ECG 22a. From these morphology matches, a diagnosis of 12-lead ECG 32(1) as a left bundle branch block for example and a diagnosis of 12-lead ECG 32(2) as a left bundle branch block for example improves upon the electrocardiographer ability to render an accurate diagnosis of the ECG morphology of the QRS in leads V1 through V4 of 12-lead ECG 22a as a left bundle branch block.

Figure 3:
FIG. 3 illustrates exemplary embodiments of a subject ECG and a pair of diagnostic ECGs in accordance with the inventive principles of the present disclosure.
Figure 3:
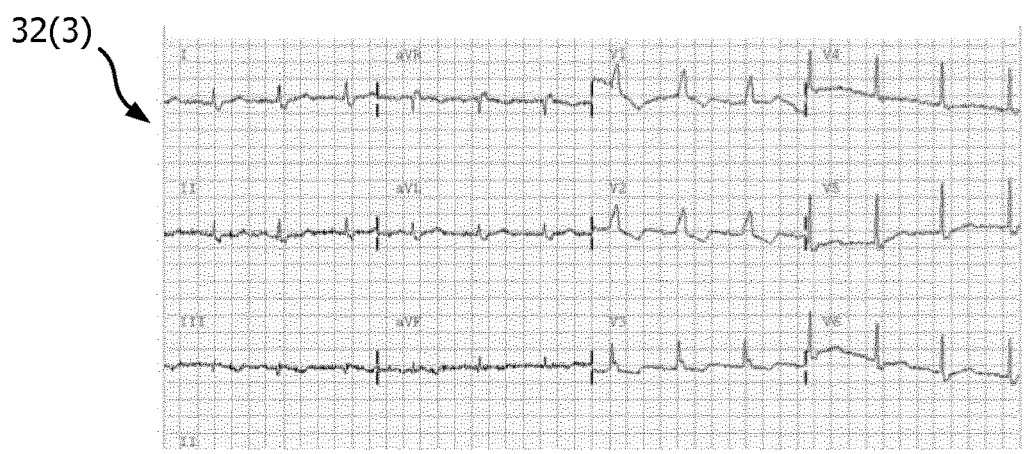
Figure 3:
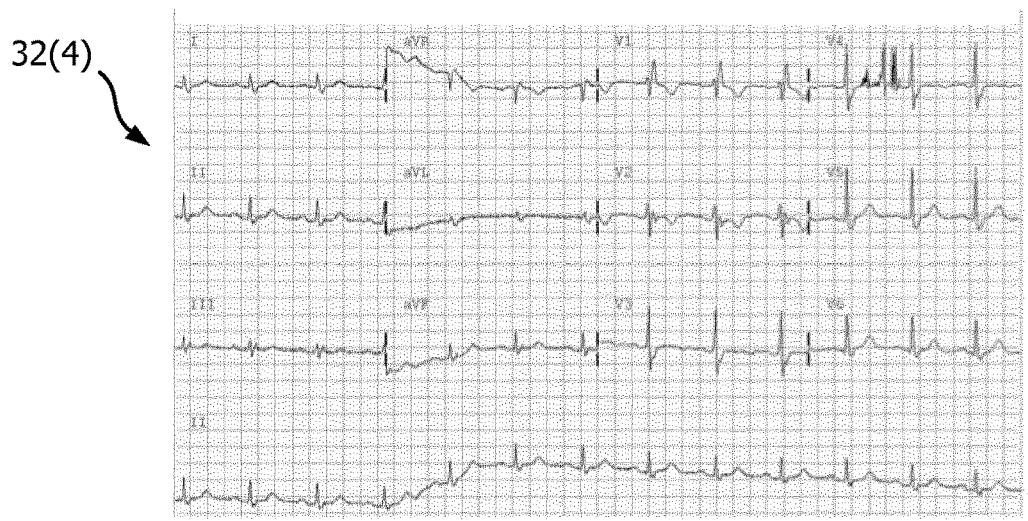

By further example, FIG. 3 illustrates an exemplary 12-lead ECG 22b of a subject electrocardiogram having an ECG morphology that could be interpreted, algorithmically and/or via by annotation, as a right bundle branch block with or without ischemia (i.e., ST-segment depression and inverted T-waves). These possible interpretations of 12-lead ECG 22b make it difficult for an electrocardiographer to render a diagnosis of the morphology of 12-lead ECG 22b, particularly an inexperienced electrocardiographer.

FIG. 3 further illustrates 12-lead ECGs 32(3) and 32(4) of a pair of diagnostic electrocardiograms designated by the electrocardiograph, from a sample database of roughly 10,000 diagnostic electrocardiograms, as a morphology match in view of abnormal shapes of the QRS in leads V1 through V4 of 12-lead ECGs 32(1) and 32(2) essentially being the same as the ECG morphology of the QRS in leads V1 through V4 of 12-lead ECG 22b. From these morphology matches, a diagnosis of 12-lead ECGs 32(3) and 32(4) as a right bundle branch block with ischemia for example improves upon the electrocardiographer's ability to render an accurate diagnosis of the ECG morphology of the QRS in leads V1 through V4 of 12-lead ECG 22b as a right bundle branch block with ischemia.

As one having ordinary skill in the art of the present disclosure shall appreciate in view of the teachings of FIGS. 1A and 1B, whatever an interpretation of the subject electrocardiogram, the present disclosure provides confidence in an electrocardiographer in rendering a diagnosis of the subject electrocardiogram when an interpretation of the subject electrocardiogram characteristically match a diagnosis of one or more diagnostic electrocardiograms.

Figure 4:
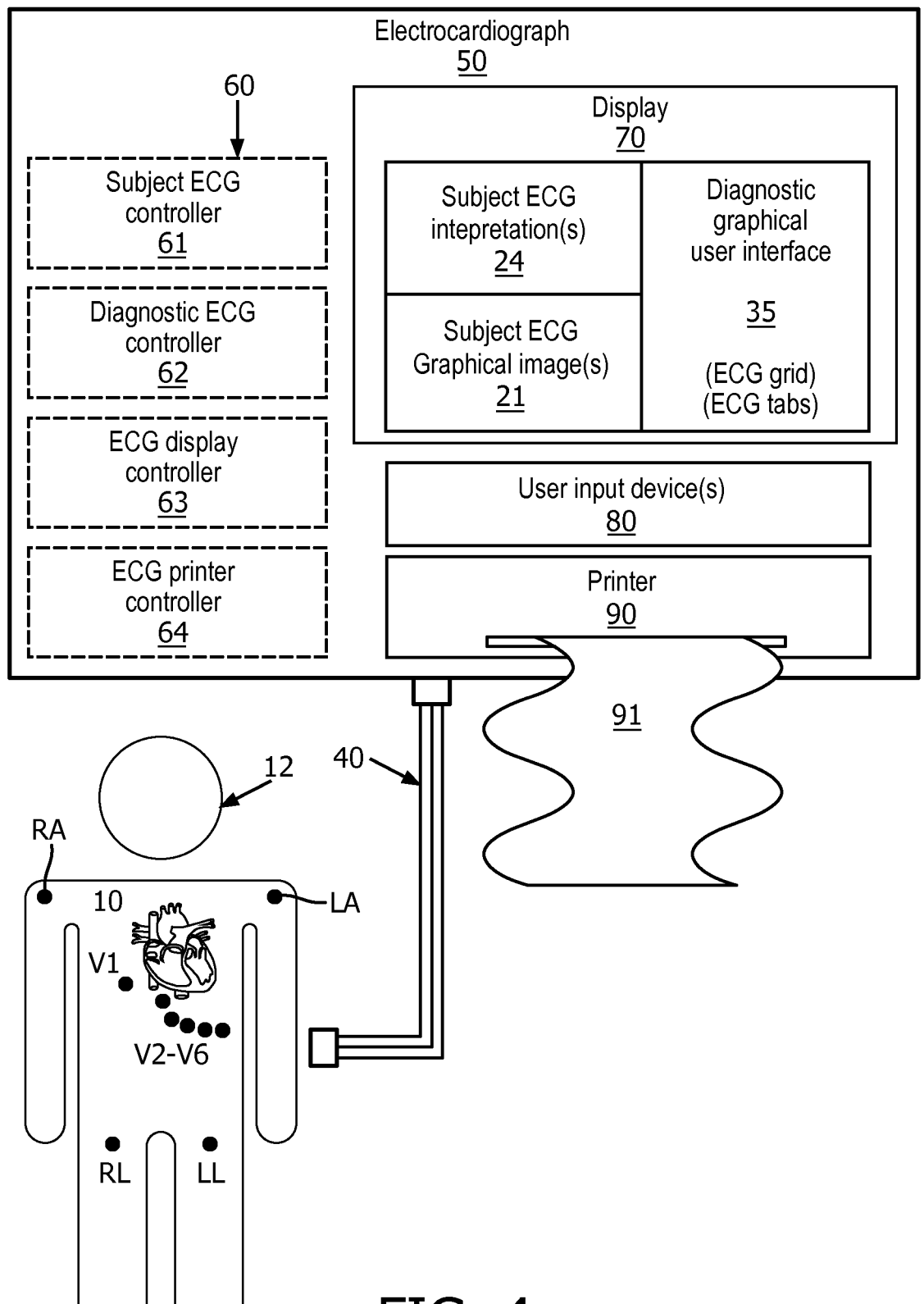
FIG. 4 illustrates an exemplary embodiment of a diagnostic electrocardiograph in accordance with the inventive principles of the present disclosure.

To further facilitate an understanding of the present disclosure, the following description of FIG. 4 teaches inventive principles of a diagnostic electrocardiograph of the present disclosure. From this description, those having ordinary skill in the art will appreciate how to apply the inventive principles of the present disclosure for making and using numerous and various embodiments of a diagnostic electrocardiograph of the present disclosure.

Referring to FIG. 4, a diagnostic electrocardiograph 50 of the present disclosure employs a control network 60, a display 70, user input device(s) 80 (e.g., button(s), dial(s), touchpad, etc.) and a printer 90. Diagnostic electrocardiograph 50 may further employ one or more additional devices as known in the art of the present disclosure (e.g., a speaker and LED status indicators).

Diagnostic electrocardiograph 50 is linked to and/or incorporates any necessary hardware/software interface to a cable connector 40 for receiving on or more electrode signal(s) from an electrode lead system connected to a subject 12 for monitoring and/or testing a subject heart 10 (e.g., a standard 12-lead system like a Mason-Likar lead system as shown or a reduced lead system like the EASI lead system).

Control network 60 includes a subject ECG controller 61, a diagnostic ECG controller 62, a ECG display controller 63 and a ECG printer controller 64 linked to or housed within diagnostic electrocardiograph 50 as shown. In practice, controllers 61-64 may be integrated to a designed degree and/or segregated as shown. Also in practice, control network 60 may include one or more additional controllers as known in the art of the present disclosure (e.g., a canopy controller, an automatic defibrillation controller, etc.).

Subject ECG controller 61 is structurally configured as known in the art of the present disclosure for controlling a generation of a subject electrocardiogram from the electrode signal(s) (e.g., a subject ECG controller commercially employed by a Holter monitor, a IntelliVue monitor, a HeartStart MRx defibrillator and a HeartStart XL defibrillator). In practice, the generation of the subject electrocardiogram by subject ECG controller 61 includes a generation of one or more subject ECG graphical image(s) (e.g., subject graphical ECG image(s) 21 of FIG. 1A), and may further includes an algorithmic generation and/or electrocardiographer annotation of one or more interpretations of the subject ECG graphical image(s) (e.g., subject interpretation(s) 24 of FIG. 1A.

Diagnostic ECG controller 62 is structurally configured in accordance with the inventive principles of the present disclosure for designating one or more diagnostic electrocardiograms (e.g., diagnostic electrocardiograms 30 of FIG. 1B) as an morphology match to the subject electrocardiogram as will be further exemplarily described herein in connection with FIGS. 5-9.

ECG display controller 63 is structurally configured as known in the art of the present disclosure for displaying electrocardiograms (e.g., an ECG display controller commercially employed by a Holter monitor, a IntelliVue monitor, a HeartStart MRx defibrillator and a HeartStart XL defibrillator) and for displaying a graphical user interface for accessing the diagnostic electrocardiograms in accordance with the inventive principles of the present disclosure. In practice, the display of the electrocardiograms by ECG display controller 63 may include:

1. a user customization of a view of the subject ECG graphical images via user input device(s) 80 and/or a graphical user interface (not shown);
2. a user annotation of an algorithmic interpretation of a subject electrocardiogram via user input device(s) 80 and/or a graphical user interface (not shown); and/or
3. a user selection of a diagnostic electrocardiogram to be displayed via user input device(s) 80 or a diagnostic graphical user interface 25 having a grid of large thumbnail images of diagnostic electrocardiograms ("ECG grid"), a tabbed organization of diagnostic electrocardiograms ("ECG tabs") or any other icon suitable for a managed review of diagnostic electrocardiograms.

ECG printer controller 64 is structurally configured as known in the art of the present disclosure for printing electrocardiograms via user input device(s) 80 and/or a graphical user interface (not shown) (e.g., an ECG printer controller commercially employed by a Holter monitor, a IntelliVue monitor, a HeartStart MRx defibrillator and a HeartStart XL defibrillator).

Figure 5:
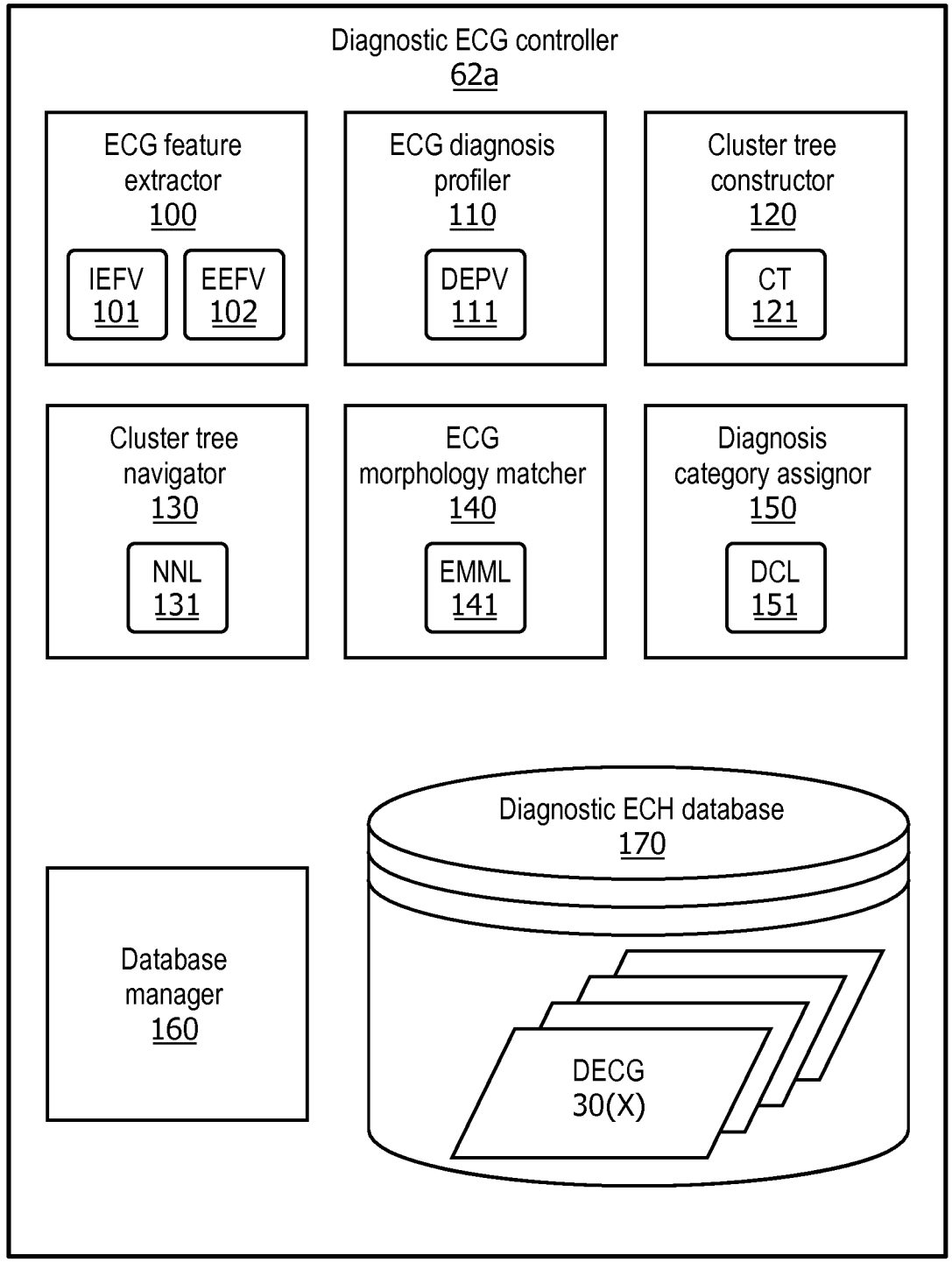
FIG. 5 illustrates an exemplary embodiment of a diagnostic ECG controller in accordance with the inventive principles of the present disclosure.

To facilitate a further understanding of the present disclosure, the following description of FIG. 5 teaches inventive principles of a diagnostic ECG controller of the present disclosure. From this description, those having ordinary skill in the art will appreciate how to apply the inventive principles of the present disclosure for making and using numerous and various embodiments of a diagnostic ECG controller of the present disclosure.

Figure 6:
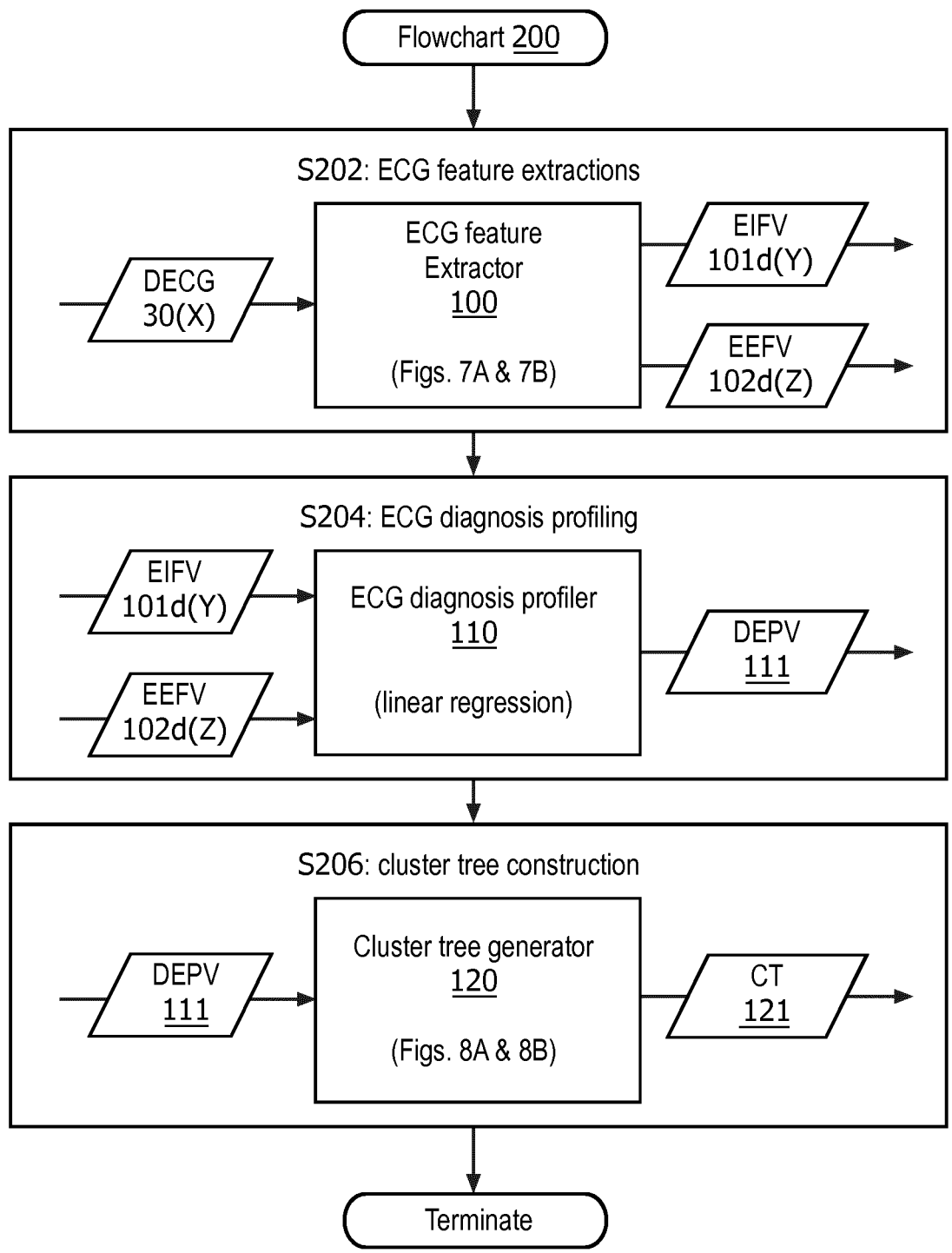
FIG. 6 illustrates a flowchart representative of an exemplary embodiment of a diagnostic electrocardiograph training method in accordance with the inventive principles of the present disclosure.
Figure 7:
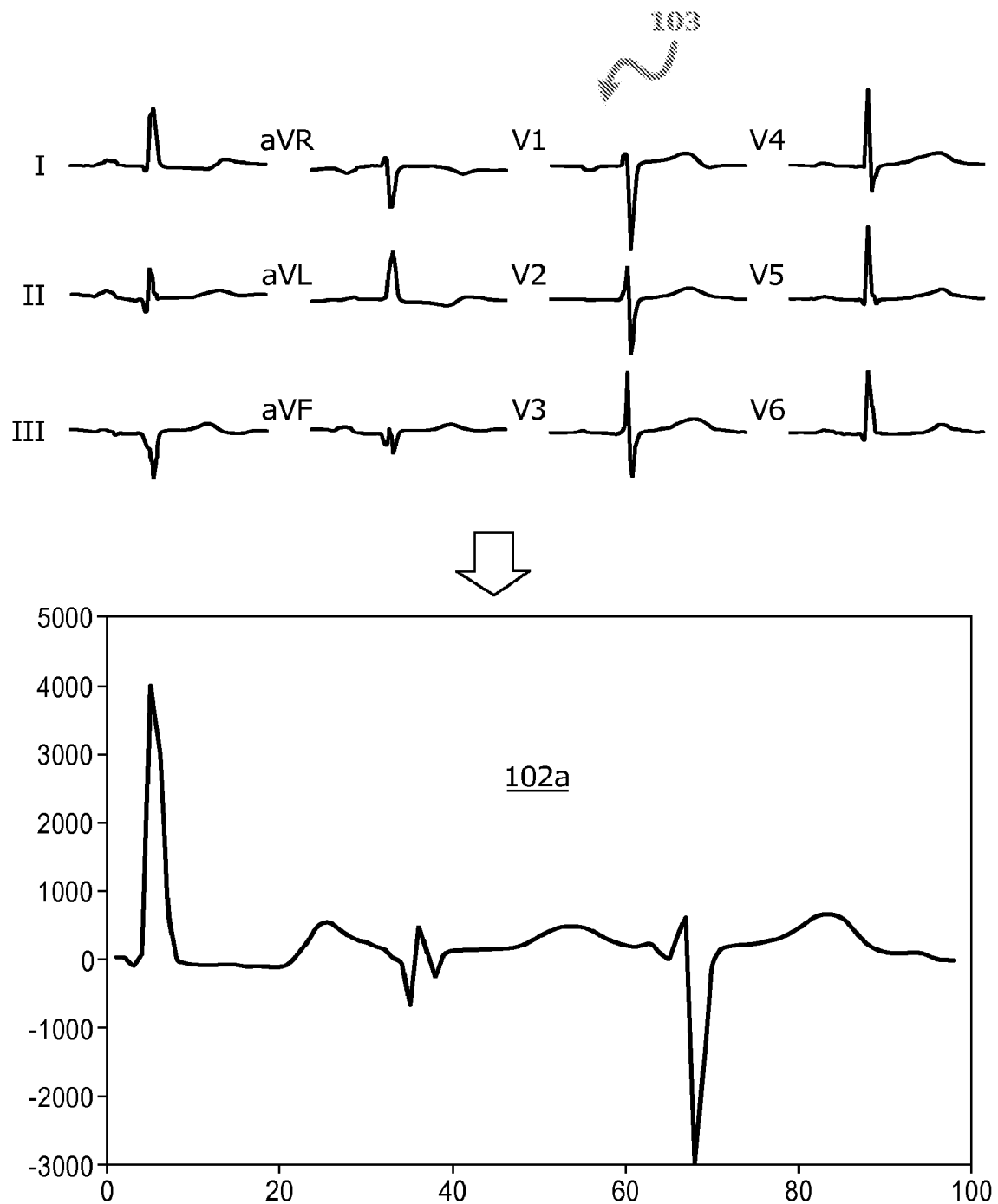
FIG. 7 illustrates an exemplary embodiment of a generation of a vector loop version of an ECG feature vector in accordance with the inventive principles of the present disclosure.
Figure 8A:
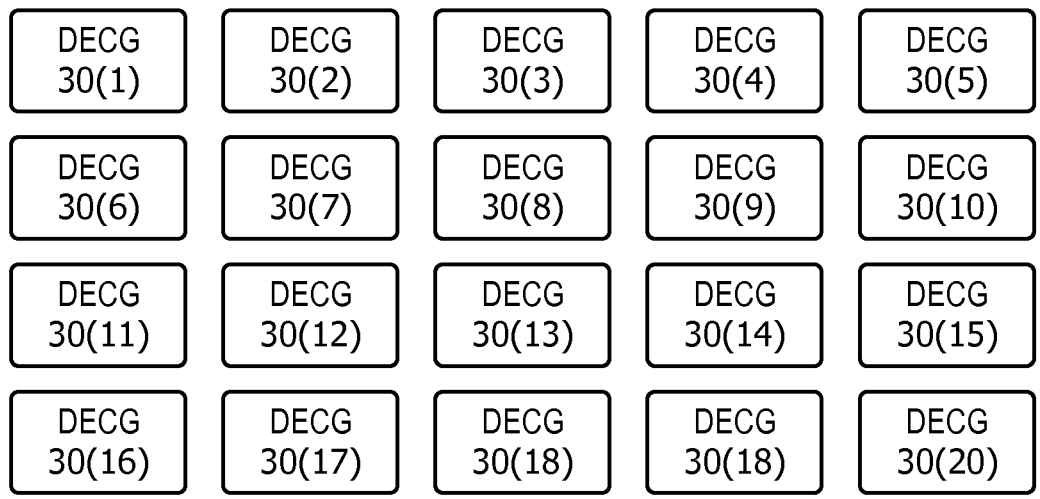
FIGS. 8A and 8B illustrate an exemplary embodiment of a construction of a cluster tree in accordance with the inventive principles of the present disclosure.
Figure 8A:
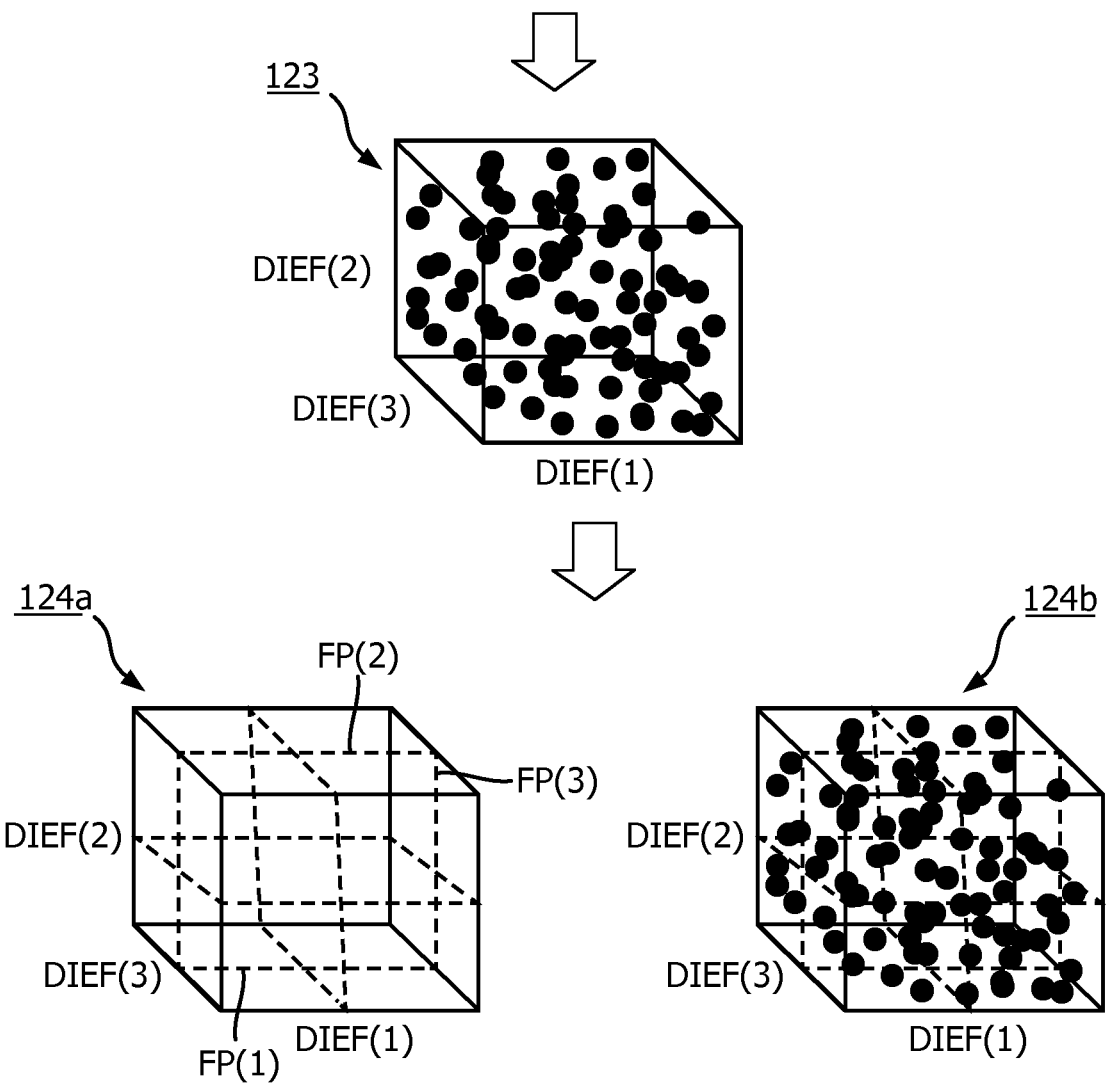

Referring to FIG. 5, an embodiment 62a of diagnostic ECG controller 62 (FIG. 4) employs an ECG feature extractor 100, an ECG profile builder 110, and a cluster tree constructor 120 for purposes of training diagnostic ECG controller 62a as will be further described herein in connection with FIGS. 6-8. Diagnostic ECG controller 62 further employs a cluster tree navigator 130, an ECG morphology matcher 140 and a diagnosis category assignor 150 for operating diagnostic ECG controller 62a for monitoring/testing purposes as will be further described herein in connection with FIGS. 8 and 9. For both training and monitoring/testing purposes, diagnostic ECG controller 62a may further employ a database manager 160 and a diagnostic ECG database 170 as shown, or alternatively be in communication with database manager 160 for purposes of accessing diagnostic ECG database 170.

Diagnostic ECG database 170 stores an X number of diagnostic electrocardiograms 30 as shown. As previously described herein, each diagnostic electrocardiogram 30 is generated from a previous diagnosed ECG monitoring and/or testing of a non-subject heart (i.e., a diagnosed heart). Each diagnostic electrocardiogram 30 includes graphical image(s), such as, for example, a 12-lead ECG, an ECG waveform and/or a vectorcardiogram. Each diagnostic electrocardiogram 30 further includes an ECG diagnosis by an electrocardiographer of an ECG morphology of the graphical image(s) with each ECG diagnosis being directed to one or more formalized statements by an electrocardiographer of an ECG morphology of corresponding graphical image(s) as would be understood by those skilled in the art of the present disclosure.

Still referring to FIG. 5, ECG feature extractor 100 is structurally configured with hardware, software, firmware and/or circuitry for processing an electrocardiogram, subject or diagnostic, to calculate an inexpensive ECG feature vector ("IEFV") 101 from the electrocardiogram with IEFV 101 including a m number of inexpensive ECG features, $m \geq 1$. Examples of an inexpensive ECG feature include, but are not limited to, QRS axis, QRS duration, QT interval, Q/R/S wave amplitudes, ST-segment amplitude, T-wave amplitude and a vector loop. In practice, ECG feature extractor 100 may implement any technique for calculating inexpensive ECG features as known in the art of the present disclosure.

ECG feature extractor 100 is further structurally configured with hardware, software, firmware and/or circuitry for processing pairings of electrocardiograms, subject-diagnostic and/or diagnostic-diagnostic, and/or for processing pairings of inexpensive ECG feature vectors 101, subject-diagnostic or diagnostic-diagnostic, to calculate expensive ECG feature vectors ("EEFV") 102 between the electrocardiogram pair with EEFV 101 including a q number of expensive ECG features, $q \geq 1$. Examples of an expensive ECG feature include, but are not limited to, a template matching, a cross correlation and a RMS difference between the electrocardiogram pair. In practice, ECG feature extractor 100 may implement any technique for calculating expensive ECG features as known in the art of the present disclosure.

ECG diagnosis profiler 110 is structurally configured with hardware, software, firmware and/or circuitry for processing an inexpensive ECG feature vector 101 for each diagnostic electrocardiogram 30 and an expensive ECF feature vector 102 of each pairing of electrocardiograms 30 to build a diagnostic ECG profile vector ("DEPV") 111 including a n number of inexpensive ECG features best representative of the interpretative prowess of expensive ECG features as known in the art of the present disclosure, $m \geq n \geq 1$ (i.e., diagnostic inexpensive ECG features). In practice, ECG diagnosis profiler 110 may implement any technique for determining which inexpensive ECG features best model the expensive ECG features as known in the art of the present disclosure including, but not limited to, a linear regression of IEFVs 101 and EEFVs 102.

Cluster tree constructor 120 is structurally configured with hardware, software, firmware and/or circuitry for processing diagnostic ECG profile vector 111 to construct a cluster tree ("CT") 121 of nodes and leafs established by the profiled inexpensive ECG features. Each node will be associated with one of the profiled inexpensive ECG features and corresponding threshold value. Each leaf will be associated with one or more diagnostic electrocardiograms 30. In practice, cluster tree constructor 120 may implement any technique for constructing clustering tree 121 including, but not limited to, constructing a decision tree from a partitioned data space derived from diagnostic ECG profile vector 111 into cluster (or dense) regions and empty (or sparse) regions formed by a partitioned clustering or a hierarchical clustering.

Cluster tree navigator 130 is structurally configured with hardware, software, firmware and/or circuitry for processing inexpensive ECG feature vector 101 of a subject electrocardiogram to navigate the nodes of cluster tree 121 until reaching a leaf whereby cluster tree navigator 130 generates a nearest neighbor listing ("NNL") 131 of all of the diagnostic electrocardiogram(s) 30 associated with the reached leaf.

ECG morphology matcher 140 is structurally configured with hardware, software, firmware and/or circuitry for processing nearest neighboring listing 131 to designate one or more of the nearest neighbor diagnostic electrocardiograms 30 as an morphology match to the subject electrocardiogram whereby ECG morphology matcher 140 generates a morphology match listing ("EMML") 141 of each designated nearest neighbor diagnostic electrocardiogram 30. In practice, ECG morphology matcher 140 may implement any known technique for determining any similarity of ECG morphologies between the subject electrocardiogram and each nearest neighbor diagnostic electrocardiogram.

Diagnosis category assignor 150 is structurally configured with hardware, software, firmware and/or circuitry for processing morphology match listing 141 to assign each morphology matched diagnostic electrocardiogram to one of numerous diagnostic categories with each diagnostic category being representative of a particular diagnostic assessment of a diagnostic electrocardiogram. Examples of a diagnostic category include, but are not limited to, left bundle branch block (LBBB), right bundle branch block (RBBB), left ventricular hypertrophy, right ventricular hypertrophy, left anterior fascicular block, acute myocardial infarction and prior myocardial infarction.

Diagnosis category assignor 150 generates a diagnostic category listing ("DCA") of each diagnostic category and associated diagnostic electrocardiograms to provide a diagnostic assessment of the subject cardiogram. In practice, diagnosis category assignor 150 may further determine a probability that each listed diagnostic category represents an accurate diagnostic assessment of the subject electrocardiogram.

To facilitate a further understanding of the present disclosure, the following description of FIG. 6 teaches inventive principles of a diagnostic electrocardiograph training method of the present disclosure. From this description, those having ordinary skill in the art will appreciate how to apply the inventive principles of the present disclosure for setting up and using numerous and various embodiments of diagnostic electrocardiograph training methods of the present disclosure.

Referring to FIG. 6, a flowchart 200 is representative of a diagnostic electrocardiograph training method of the present disclosure executed during a training phase of diagnostic ECG controller 62a (FIG. 5). In practice, diagnostic ECG database 170 will typically include thousands, even millions, of a large morphology variation of diagnostic electrocardiograms 30. Flowchart 200 facilitates a partitioning of inexpensive ECG features of diagnostic electrocardiograms 30 that are best representative of possible interpretations of the morphology of diagnostic electrocardiograms 30.

Still referring to FIG. 6, a stage S202 of flowchart 200 encompasses ECG feature extractor 100 processing a set of diagnostic electrocardiograms 30 to calculate a Y number of inexpensive ECG feature vectors 101, $X \geq Y \geq 1$, (e.g., a Y-dimensional vector of inexpensive ECG features or alternatively a vector loop) and a Z number of expensive ECG feature vectors 102, $Z \geq 1$.

More particular to 12-lead electrocardiogram, in practice inexpensive ECG feature vector 101 would be made of a processed version of the lead signals instead of a set of measurements (e.g., R-wave amplitude and QRS duration). Since the number of points in the representative beat (or average beat made up of similar shaped beats, excluding noisy and ectopic beats) may be very big for an inexpensive feature vector (e.g., 12 leads×500 points per lead), the number of points should be reduced if possible. This implementation may use (2) methods to reduce the number of points in an inexpensive ECG feature vector while still retaining the unique morphology information. First, the number of points would be reduced by changing from 12-leads which contains a fair amount of redundant information to three (3) orthogonal leads with a 12-lead ECG to Frank lead vectorcardiogram transform. This is a 4:1 reduction in points. Second, the number of points would be further reduced by using the approximation given by a multilevel wavelet decomposition. Using the approximation from the 4th level decomposition, the final number of points in the inexpensive ECG feature vector reduced to roughly 100.

FIG. 7 illustrates an exemplary transformation of a 12-lead representative beat 103 into a Frank lead representative beat 102a to be utilized as an inexpensive ECG feature vector 101 of an electrocardiogram. The Frank lead X, Y and Z signals are used to generate two dimensional vector loops from pairs of the X, Y and Z signals. In practice, pairs of vectorcardiograms may also be utilized to generate expensive ECG feature vectors 102.

In practice for stage S202, the entire database 170 of diagnostic electrocardiograms 30 or a subset thereof may be processed by ECG feature extractor 100 dependent on various factors.

For example, the calculation of the expensive ECG feature vectors 102 in practice may involve a sample of a comparison for every diagnostic electrocardiogram 30 to every other electrocardiogram 30, or a random sample for a subset of diagnostic electrocardiograms 30, or targeted groups of diagnostic electrocardiograms 30 which are expected to be within the same diagnostic groups.

Additionally, if diagnostic ECG database 70 is relatively large relative to the processing power of diagnostic ECG controller 62a (FIG. 5), then diagnostic electrocardiograms 30 may be segmented in practice by age groups and/or gender to limit a size of a resulting cluster tree.

Furthermore, diagnostic electrocardiograms 30 processed by ECG feature extractor 100 may be based in practice only on select electrocardiographers with many years of experience or proven excellence in ECG reading accuracy. This omits diagnostic electrocardiograms 30 from less experienced electrocardiographers.

Even further, those having ordinary skill in the art of the present disclosure will recognize a ECG morphology for a stress test of a subject heart is different from a morphology of a resting diagnostic ECG of the same subject heart. Nonetheless, the present disclosure is equally applicable to a relaxed monitoring and a stress testing of the same subject heart. Consequently, in practice, diagnostic ECG database 70 may be divided into a resting ECG training database resulting in a resting ECG cluster tree and a stress test training database resulting in a stress testing ECG cluster tree.

Still referring to FIG. 6, a stage S204 of flowchart 200 encompasses ECG diagnosis profiler 110 processing the Y number of inexpensive ECG feature vectors 101 and the Z number of expensive ECG feature vectors 102 to build diagnostic ECG profile vector ("DEPV") 111 including a n number of inexpensive ECG features best representative of the interpretative prowess of expensive ECG features.

In one embodiment of stage S204, ECG diagnosis profiler 110 implements a linear regression or another similar method to determine which inexpensive ECG features best model the expensive ECG features. For this embodiment, the dependent variables are the expensive ECG features and the independent variables are the differences in the inexpensive ECG features. The training set for this linear regression operation is the set of differences in ECG features for each diagnostic electrocardiogram 30 compared to other diagnostic electrocardiogram 30 in the training set. In the simplest case, linear regression is fitting a line to a scatter plot of points in view of having one dependent variable and multiple independent variables. After fitting a line to the data, i.e. training, the dependent variable is a linear function of the independent variables or features. The following is a model equation [1]:

$$Y = b0 + b1*x1 + b2*x2 + \ldots + bn*xn. \quad [1]$$

where Y is the dependent variable, where x1, x2, . . . , xn are the independent variables, and b0, b1, . . . , bn are the coefficients determined in the training operation.

In the extreme case, the set of rows (each row is a trial and each column is a feature) is a comparison of every diagnostic electrocardiogram 30 to every other diagnostic electrocardiogram 30.

After the linear regression model is calculated, ECG diagnosis profiler 110 will generate a vector of inexpensive ECG features with a low p-value (i.e., inexpensive ECG feature(s) making a significant contribution to the dependent variable as would be recognized by one skilled in the art of the present disclosure).

Still referring to FIG. 6, a stage S206 of flowchart 200 encompasses cluster tree generator 120 processing ECG profile vector 111 to construct cluster tree 121.

In one embodiment of stage S206, cluster tree generator 120 implements a nearest neighbor algorithm having a k-d tree, which stands for k-dimensional tree. K dimensions means there are k features used in the clustering operation. This is a binary tree. Each node in the tree has two nodes below, a left node and a right node. Below these nodes are more nodes therefore each split into the left and right results in a left and right sub-tree. The termination of a branch of the tree, a leaf, is a k-dimensional data point. The left and right subtrees represent a splitting of all points below by a plane. Since there are k-dimensions, it is a hyperplane in general. As you move from the root node at the top, down level after level of the tree, the splitting at each level corresponds to splitting based on just one of the k features. Usually, the split happens about the median of that feature. All points for the subtree with a value of the particular feature higher than the median value for the subtree go on one side of the hyperplane, all the other points go to the other side of the hyperplane. Going down the levels of the tree, the splitting rotates through the features meaning that the splitting for the root node is based on the first feature, the splitting at the next level uses the next feature and so forth.

FIG. 8A shows a clustering example of stage S206 involving twenty (20) diagnostic electrocardiograms 30 whereby three (3) diagnostic inexpensive ECG features DIEF have been determined to be best representative of the interpretative prowess of expensive ECG features (e.g., QRS axis, QRS duration and QT interval). The diagnostic inexpensive ECG features DIEF of the twenty (20) diagnostic electrocardiograms 30 are clustered within a three-dimensional data space 123 whereby a partitioning clustering is applied by cluster tree generator 120 to yield a partitioned data space 124 via feature partitions FP(1) through FP (3) (e.g., a partition based on a median or mode of each diagnostic inexpensive ECG feature).

Figure 8B:
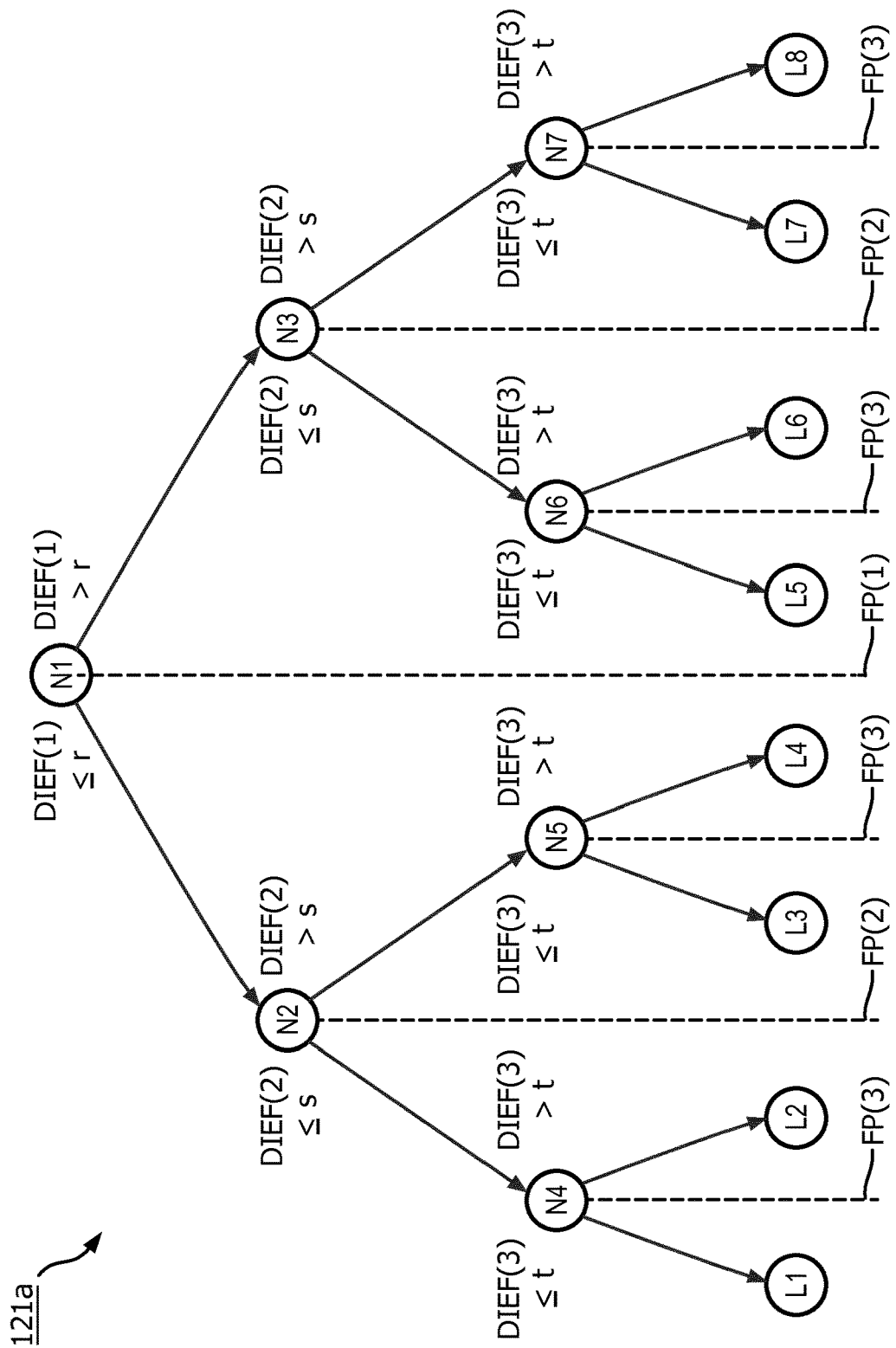

FIG. 8B shows a construction of a clustered decision tree 121a from partitioned data space 124. Clustered decision tree 121a include nodes N1 through N7, and leaf L1 through leaf 8. Node N1 is associated with diagnostic inexpensive ECG feature DIEF(1) having a median or mode value r. Nodes N2 and N3 associated with diagnostic inexpensive ECG feature DIEF(2) having a median or mode value s.

Nodes N4 through N7 are associated with diagnostic inexpensive ECG feature DIEF(3) having a median or mode value t.

Each leaf is associated with one or more of the twenty (20) diagnostic electrocardiograms 30 (FIG. 7A). For a simple example, leaf L1 may be associated with diagnostic electrocardiograms 30(1) through 30(3). Leaf L2 may be associated with diagnostic electrocardiograms 30(4) and 30(5). Leaf L3 may be associated with diagnostic electrocardiograms 30(6) through 30(9). Leaf L4 may be associated with diagnostic electrocardiograms 30(10). Leaf L5 may be associated with diagnostic electrocardiograms 30(11) and 30(12). Leaf L6 may be associated with diagnostic electrocardiograms 30(13) through 30(15). Leaf L7 may be associated with diagnostic electrocardiograms 30(16) through 30(18). Leaf L8 may be associated with diagnostic electrocardiograms 30(19) and 30(20).

Those skilled in the art of the present disclosure will appreciate flowchart 200 will typically involve a processing of thousands, if not millions, of diagnostic electrocardiograms 30 and FIGS. 8A and 8B were provided to demonstrate a simple example to facilitate an understanding of stage S206.

Figure 9:
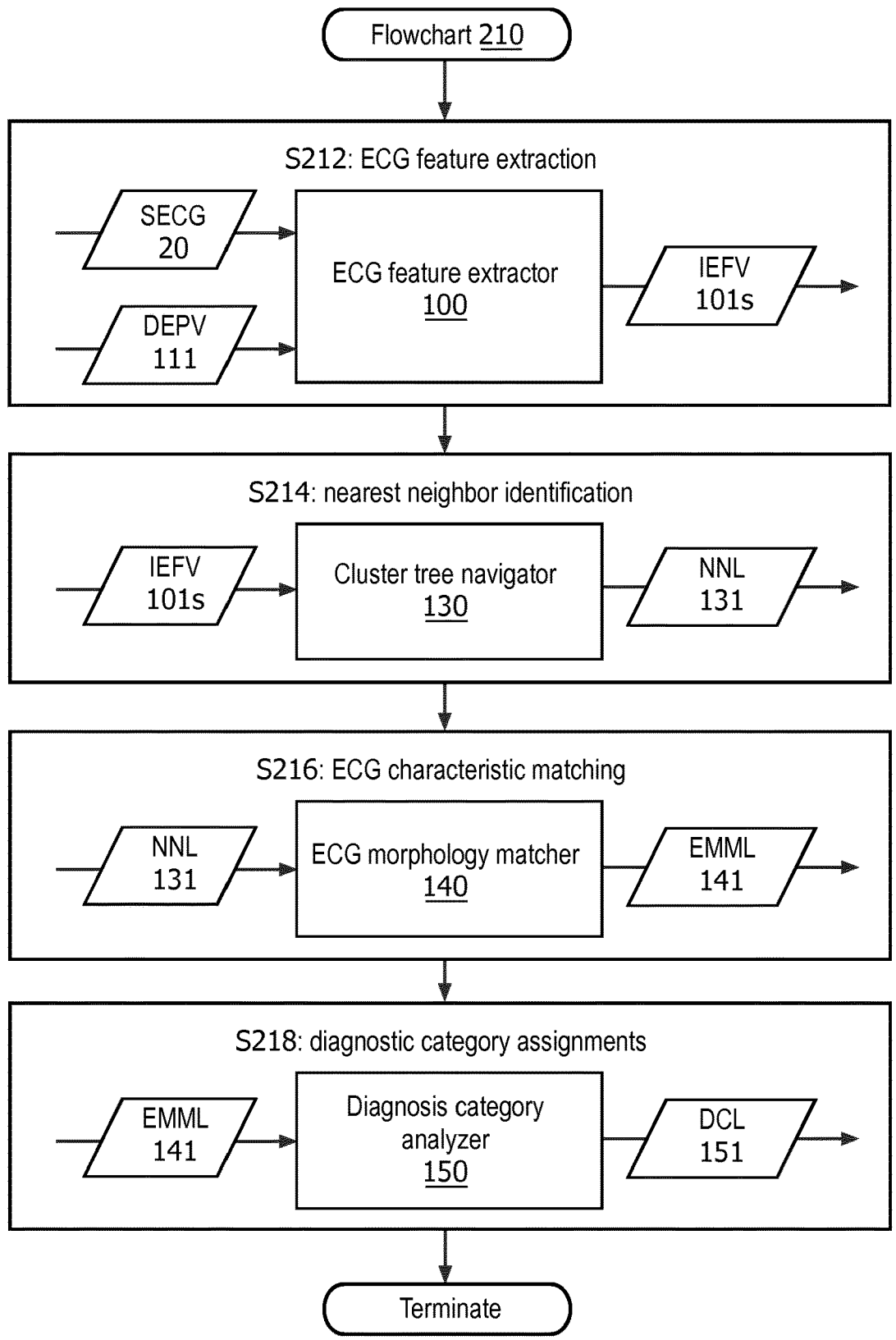
FIG. 9 illustrates a flowchart representative of an exemplary embodiment of a diagnostic electrocardiograph operational method in accordance with the inventive principles of the present disclosure.

To facilitate a further understanding of the present disclosure, the following description of FIG. 9 teaches inventive principles of a diagnostic electrocardiogram operating method of the present disclosure. From this description, those having ordinary skill in the art will appreciate how to apply the inventive principles of the present disclosure for setting up and using numerous and various embodiments of diagnostic electrocardiogram operation methods of the present disclosure.

Referring to FIG. 9, a flowchart 210 is representative of a diagnostic electrocardiogram assessment method of the present disclosure executed during an activation phase of diagnostic ECG controller 62a (FIG. 5). Flowchart 210 facilitates a diagnostic assessment of a subject electrocardiogram.

Still referring to FIG. 9, a stage S212 of flowchart 210 encompasses ECG feature extractor 100 processing a subject electrocardiogram (e.g., subject electrocardiogram 20 shown in FIG. 1A) and diagnostic ECG profile vector 111 to generate an inexpensive ECG feature vector 101s corresponding to diagnostic ECG profile vector 111. For example, in the context of FIGS. 8A and 8B, ECG feature extractor 100 generates an inexpensive ECG feature vector 101s including diagnostic inexpensive ECG features DIEF(1) through DIEF(3).

A stage S214 of flowchart 210 encompasses cluster tree navigator 130 processing inexpensive ECG feature vector 101s to navigate the nodes of cluster tree 121 until reaching a leaf whereby cluster tree navigator 130 generates a nearest neighbor listing ("NNL") 131 of all of the diagnostic electrocardiogram(s) 30 associated with the reached leaf. For example, in the context of FIGS. 8A and 8B, cluster tree navigator 130 may reach leaf L1 and generates a nearest neighbor listing 131 including diagnostic electrocardiograms 30(1) through 30(3).

A stage S216 of flowchart 210 encompasses ECG morphology matcher 140 processing nearest neighboring listing 131 to generate an morphology match listing ("EMML") 141 of each designated nearest neighbor diagnostic electrocardiogram 30.

In one embodiment of stage S216, ECG morphology matcher 140 calculates the expensive ECG features between the subject electrocardiogram and each nearest neighbor diagnostic electrocardiogram 30 (e.g., a template match, cross correlation or RMS error), and determines a cross correlation between the average beat of the subject electrocardiogram and the average beats of the nearest neighbor diagnostic electrocardiograms resulting in a vector of cross correlation numbers. ECG morphology matcher 140 chooses the subset of nearest neighbor diagnostic electrocardiograms by sorting the cross correlation vector from highest to lowest and selecting the subset with the highest cross correlation(s) (i.e., most similar to the subject electrocardiogram).

For example, in the context of FIGS. 8A and 8B, ECG morphology matcher 140 may designate diagnostic electrocardiograms 30(1) and 30 (2) as morphology matches.

A stage S218 of flowchart 210 encompasses diagnosis category assignor processing morphology match listing 141 to assign each matched diagnostic electrocardiogram to a diagnostic category with each diagnostic category being representative of a particular diagnostic assessment of a diagnostic electrocardiogram and to determine a probability that each listed diagnostic category represents an accurate diagnostic assessment of the subject electrocardiogram.

In one embodiment of stage S218, the probability of diagnostic category is calculated as the frequency of the notation of that diagnostic category for the morphology matched subset of nearest neighbors. Specifically, a diagnosis of each morphology matched nearest neighbor is mapped to a broader diagnostic category. The number of times that each diagnostic category is noted is divided by the number of diagnostic electrocardiograms in the morphology matched set of nearest neighbors. That ratio is an estimate of the probability.

For example, in the context of FIGS. 8A and 8B, diagnostic electrocardiograms 30(1) and 30(2) may be mapped to a left bundle branch block and diagnostic electrocardiogram 30(2) may be further mapped to a left ventricular hypertrophy. As such, the probability of the subject electrocardiogram may be exhibiting left bundle branch block would be 66% and the probability of the subject electrocardiogram may be exhibiting left ventricular hypertrophy would be 33%.

Upon completion of flowchart 210, the morphology matched set of nearest neighbors are presented to the electrocardiographer in a grid of large thumbnail images, or a tabbed organization or some other icon that allows quick change from one diagnostic electrocardiogram to the next for fast review of all diagnostic electrocardiograms for the morphology matched subset of nearest neighbors.

Referring to FIGS. 1-9, those having ordinary skill in the art will appreciate numerous benefits of the inventions of the present disclosure including, but not limited to, an improvement of electrocardiographs in diagnostically assessing a subject electrocardiogram.

The present disclosure disclosed herein has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Further, as one having ordinary skill in the art shall appreciate in view of the teachings provided herein, features, elements, components, etc. disclosed and described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and exemplary embodiments of the present disclosure, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar functionality, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of diagnostic electrocardiographs and operating methods thereof, (which embodiments are intended to be illustrative and not limiting), it is noted that modifications and variations can be made by persons having ordinary skill in the art in view of the teachings provided herein, including the appended Figures and claims. It is therefore to be understood that changes can be made in/to the preferred and exemplary embodiments of the present disclosure which are within the scope of the present disclosure and exemplary embodiments disclosed and described herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A diagnostic electrocardiogram system, comprising:
    an electrode lead system for generating at least one electrode signal indicative of electrical activity of a subject heart; and
    a diagnostic electrocardiograph operable to be coupled to the electrode lead system
        wherein the diagnostic electrocardiograph is configured to communicate a subject electrocardiogram and at least one diagnosed electrocardiogram designated as a morphology match to the subject electrocardiogram,
        wherein the subject electrocardiogram is informative of at least one interpretation of ECG features derived from the electrical activity of the subject heart as indicated by the at least one electrode signal,
        wherein the at least one diagnosed electrocardiogram is accessible by the diagnostic electrocardiograph and is informative of at least one diagnosis of ECG features derived from recorded electrical activity of at least one diagnosed heart, and
        wherein a designation by the diagnostic electrocardiograph of the at least one diagnosed electrocardiogram as the morphology match to the subject electrocardiogram includes:
            the diagnostic electrocardiograph further configured to determine a probability of the at least one diagnosed electrocardiogram being representative of an accurate diagnostic assessment of the subject electrocardiogram based on a similarity between a morphology of the subject electrocardiogram and a morphology of the at least one diagnosed electrocardiogram.

2. The diagnostic electrocardiogram system of claim 1,
    wherein at least one interpretation of ECG features derived from the electrical activity of the subject heart as indicated by the at least one electrode signal includes at least one of an algorithmic interpretation and an electrocardiographer interpretation; and
    wherein the at least one diagnosis of ECG features derived from recorded electrical activity of at least one diagnosed heart includes at least one of an algorithmic diagnosis and an electrocardiographer diagnosis.

3. The diagnostic electrocardiogram system of claim 1,
    wherein the diagnostic electrocardiograph includes a subject electrocardiogram controller and a diagnostic electrocardiogram controller;
    wherein the subject electrocardiogram controller, responsive to the generation of the at least one electrode signal by the electrode lead system, is configured to control a generation of the subject electrocardiogram; and
    wherein the diagnostic electrocardiogram controller, responsive to the generation of the subject electrocardiogram by the subject electrocardiogram controller, is configured to control the designation of the at least one diagnosed electrocardiogram as the morphology match to the subject electrocardiogram.

4. The diagnostic electrocardiogram system of claim 3, wherein the control by the diagnostic electrocardiogram controller of the designation of the at least one diagnosed electrocardiogram as the morphology match to the subject electrocardiogram includes:
    the diagnostic electrocardiogram controller further configured to access a cluster tree constructed from a training set of diagnosed electrocardiograms informative of a plurality of diagnoses of ECG features derived from recorded electrical activity of a plurality of diagnosed hearts; and
    the diagnostic electrocardiogram controller further configured to control a navigation of the cluster tree to designate the at least one diagnosed electrocardiogram from the training set of diagnosed electrocardiogram as the morphology match to the subject electrocardiogram.

5. The diagnostic electrocardiogram system of claim 4, wherein the control by the diagnostic electrocardiogram controller of the designation of the at least one diagnosed electrocardiogram as the morphology match to the subject electrocardiogram includes:

the diagnostic electrocardiogram controller further configured to control an assignment of the at least one diagnosed electrocardiogram into a least one diagnostic category representative of at least one diagnostic assessment of the subject electrocardiogram.

6. The diagnostic electrocardiogram system of claim 5, wherein the control by the diagnostic electrocardiogram controller of the designation of the at least one diagnosed electrocardiogram as the morphology match to the subject electrocardiogram includes:

for a plurality of diagnostic categories, the diagnostic electrocardiogram controller further configured to control a determination of an accurate diagnosis probability for each diagnostic category.

7. The diagnostic electrocardiogram system of claim 4, wherein a navigation of the cluster tree by the diagnostic electrocardiogram controller includes:

the diagnostic electrocardiogram controller further configured to generate an inexpensive ECG feature vector from an application of a diagnostic ECG profile vector to the subject electrocardiogram; and the diagnostic electrocardiogram controller further configured to derive a nearest neighbor listing of at least one diagnosed electrocardiogram from a navigation of the inexpensive ECG feature vector along the cluster tree.

8. The diagnostic electrocardiogram system of claim 7, wherein a navigation of the cluster tree by the diagnostic electrocardiogram controller further includes:

the diagnostic electrocardiogram controller further configured to calculate at least one expensive ECG feature between the subject electrocardiogram and the nearest neighbor listing of at least one diagnosed electrocardiogram; and the diagnostic electrocardiogram controller further configured to derive the designation of the at least one diagnosed electrocardiogram as the morphology match to the subject electrocardiogram from the at least one expensive ECG feature.

9. A diagnostic electrocardiograph, comprising:

a subject electrocardiogram controller, wherein the subject electrocardiogram controller, responsive to at least one electrode signal indicative of electrical activity of a subject heart, is configured to control a generation of a subject electrocardiogram informative of at least one interpretation of ECG features derived from the electrical activity of the subject heart as indicated by the at least one electrode signal; and a diagnostic electrocardiogram controller, wherein the diagnostic electrocardiogram controller, responsive to the generation of the subject electrocardiogram by the subject electrocardiogram controller, is configured to control a communication of a designation of at least one diagnosed electrocardiogram as a morphology match to the subject electrocardiogram, wherein the at least one diagnosed electrocardiogram is informative of at least one diagnosis of ECG features derived from recorded electrical activity of at least one diagnosed heart, and wherein the designation by the diagnostic electrocardiogram controller of the at least one diagnosed electrocardiogram as the morphology match to the subject electrocardiogram includes:

the diagnostic electrocardiogram controller further configured to determine a probability of the at least one diagnosed electrocardiogram being representative of an accurate diagnostic assessment of the subject electrocardiogram based on a similarity between a morphology of the subject electrocardiogram and a morphology of the at least one diagnosed electrocardiogram.

10. The diagnostic electrocardiograph of claim 9, wherein at least one interpretation of ECG features derived from the electrical activity of the subject heart as indicated by the at least one electrode signal includes at least one of an algorithmic interpretation and an electrocardiographer interpretation; and wherein the at least one diagnosis of ECG features derived from recorded electrical activity of at least one diagnosed heart includes at least one of an algorithmic diagnosis and an electrocardiographer diagnosis.

11. The diagnostic electrocardiograph of claim 9, wherein the control by the diagnostic electrocardiogram controller of the designation of the at least one diagnosed electrocardiogram as the morphology match to the subject electrocardiogram includes: the diagnostic electrocardiogram controller further configured to access a cluster tree constructed from a training set of diagnosed electrocardiograms informative of a plurality of diagnoses of ECG features derived from recorded electrical activity of a plurality of diagnosed hearts; and the diagnostic electrocardiogram controller further configured to control a navigation of the cluster tree to designate the at least one diagnosed electrocardiogram as the morphology match to the subject electrocardiogram.

12. The diagnostic electrocardiograph of claim 11, wherein the control by the diagnostic electrocardiogram controller of the designation of the at least one diagnosed electrocardiogram as the morphology match to the subject electrocardiogram includes:

the diagnostic electrocardiogram controller further configured to control an assignment of the at least one diagnosed electrocardiogram into a least one diagnostic category representative of at least one diagnostic assessment of the subject electrocardiogram.

13. The diagnostic electrocardiograph of claim 12, wherein the control by the diagnostic electrocardiogram controller of the designation of the at least one diagnosed electrocardiogram as the morphology match to the subject electrocardiogram includes:

for a plurality of diagnostic categories, the diagnostic electrocardiogram controller further configured to control a determination of an accurate diagnosis probability of each diagnostic category.

14. The diagnostic electrocardiograph of claim 11, wherein a navigation of the cluster tree by the diagnostic electrocardiogram controller includes:

the diagnostic electrocardiogram controller further configured to generate an inexpensive ECG feature vector from an application of a diagnostic ECG profile vector to the subject electrocardiogram; and the diagnostic electrocardiogram controller further configured to derive a nearest neighbor listing of at least one diagnosed electrocardiogram from a navigation of the inexpensive ECG feature vector along the cluster tree.

15. The diagnostic electrocardiograph of claim 14, wherein a navigation of the cluster tree by the diagnostic electrocardiogram controller further includes:

the diagnostic electrocardiogram controller further configured to calculate at least one expensive ECG feature between the subject electrocardiogram and the nearest neighbor listing of at least one diagnosed electrocardiogram; and the diagnostic electrocardiogram controller further configured to derive the designation of the at least one diagnosed electrocardiogram as the morphology match to the subject electrocardiogram from the at least one expensive ECG feature.

16. A diagnostic electrocardiograph method, comprising:

a diagnostic electrocardiograph designating at least one diagnostic electrocardiogram as a morphology match to a subject electrocardiogram including the diagnostic electrocardiograph determining a probability of at least one diagnosed electrocardiogram being representative of an accurate diagnostic assessment of a subject electrocardiogram based on a similarity between a morphology of the subject electrocardiogram and a morphology of the at least one diagnosed electrocardiogram, wherein the subject electrocardiogram informative of at least one interpretation of ECG features derived from the electrical activity of the subject heart as indicated by the at least one electrode signal, and wherein the at least one diagnosed electrocardiogram is informative of at least one diagnosis of ECG features derived from recorded electrical activity of at least one diagnosed heart; and the diagnostic electrocardiograph communicating the designation of the at least one diagnostic electrocardiogram as the morphology match to the subject electrocardiogram.

17. The diagnostic electrocardiograph method of claim 16, wherein the designation by the diagnostic electrocardiograph of the at least one diagnosed electrocardiogram as the morphology match to the subject electrocardiogram includes:

the diagnostic electrocardiograph accessing a cluster tree constructed from a training set of diagnosed electrocardiograms informative of a plurality of diagnoses of ECG features derived from recorded electrical activity of a plurality of diagnosed hearts; and the diagnostic electrocardiograph navigating the cluster tree to designate the at least one diagnosed electrocardiogram from the training set of diagnosed electrocardiogram as the morphology match to the subject electrocardiogram.

18. The diagnostic electrocardiograph method of claim 17, wherein the designation by the diagnostic electrocardiograph of the at least one diagnosed electrocardiogram as the morphology match to the subject electrocardiogram includes:

the diagnostic electrocardiograph assigning the at least one diagnosed electrocardiogram into a least one diagnostic category representative of at least one diagnostic assessment of the subject electrocardiogram; and for a plurality of diagnostic categories, the diagnostic electrocardiogram controller further configured to control a determination of an accurate diagnosis probability for each diagnostic category.

19. The diagnostic electrocardiograph method of claim 17, wherein the navigation of the cluster tree by the diagnostic electrocardiograph includes:

the diagnostic electrocardiograph generating an inexpensive ECG feature vector from an application of a diagnostic ECG profile vector to the subject electrocardiogram; and the diagnostic electrocardiograph deriving a nearest neighbor listing of at least one diagnosed electrocardiogram from a navigation of the inexpensive ECG feature vector along the cluster tree.

20. The diagnostic electrocardiograph method of claim 19, wherein the navigation of the cluster tree by the diagnostic electrocardiograph includes:

the diagnostic electrocardiograph calculating at least one expensive ECG feature between the subject electrocardiogram and the nearest neighbor listing of at least one diagnosed electrocardiogram; and the diagnostic electrocardiograph deriving the designation of the at least one diagnosed electrocardiogram as the morphology match to the subject electrocardiogram from the at least one expensive ECG feature.

* * * * *